United States Patent [19]

Olivier

[11] Patent Number: 5,152,747
[45] Date of Patent: Oct. 6, 1992

[54] IMPLANTABLE RESERVOIR AND BALLOON CATHETER SYSTEM

[76] Inventor: Lucien C. Olivier, Munscheidtstr. 20, 4300 Essen 13, Fed. Rep. of Germany

[21] Appl. No.: 568,464

[22] Filed: Aug. 16, 1990

[30] Foreign Application Priority Data

Aug. 16, 1989 [DE] Fed. Rep. of Germany ....... 3927001

[51] Int. Cl.⁵ .......................................... A61M 11/00
[52] U.S. Cl. ................... 604/93; 604/891.1
[58] Field of Search .............. 604/890.1, 891.1, 93, 604/96, 104, 132, 52, 53, 175, 264, 281, 282; 623/11, 17

[56] References Cited

U.S. PATENT DOCUMENTS

| | | | |
|---|---|---|---|
| 3,921,632 | 11/1975 | Bardani | 604/891.1 |
| 3,971,376 | 7/1976 | Wichterle | 604/891.1 |
| 4,572,186 | 2/1986 | Gould et al. | 604/105 X |
| 4,718,894 | 1/1988 | Lazorthes | 604/93 |
| 4,734,093 | 3/1988 | Bonello et al. | 604/95 |
| 4,820,349 | 4/1989 | Saab | 606/194 |
| 4,904,260 | 2/1990 | Ray et al. | 623/17 |
| 4,923,457 | 5/1990 | Ellingsen | 604/891.1 |
| 5,016,615 | 5/1991 | Driller et al. | 128/24 A |

Primary Examiner—John D. Yasko
Assistant Examiner—Adam J. Cermak
Attorney, Agent, or Firm—Anderson Kill Olick & Oshinsky

[57] ABSTRACT

The invention relates to a catheter system comprising a totally implantable reservoir for a treating agent, and at least one catheter connected thereto. The reservoir is designed to have a variable volume so that it can be positioned in the tissue by a small cannula needle when its volume is small and can be brought to the required internal volume in situ.

11 Claims, 2 Drawing Sheets

IMPLANTABLE RESERVOIR AND BALLOON CATHETER SYSTEM

TECHNICAL FIELD OF THE INVENTION

The invention relates to a catheter system comprising a reservoir and a catheter connected thereto for applying treating agents.

BACKGROUND OF THE INVENTION AND PRIOR ART

Before such catheter systems became known, only tubes running out through the skin of the patient were available. Of course such unnatural connections to the skin necessarily lead to the increased occurrence of infections. Furthermore they handicap the patient and can only be used for a limited period of time to give certain medicaments, for example, chemotherapeutic agents or pain killers. Patients who need to be given medicaments, some of which are aggressive, over a long period of time or repeatedly are however often advised that there is a connection, for example to the central vessels, that can be used any time in the abdominal cavity or else in the spinal cord canal. Nowadays these patients receive by way of an operation a dimensionally stable reservoir which is introduced under the skin by means of a relatively large surgical incision. This reservoir is then connected to the corresponding catheter in a vessel, the abdominal cavity or else in the spinal cord canal.

The totally implantable catheter systems known inter alia from "Deutsche Medizinische Wochenschrift" 114 (1989), pages 655 to 658 have proven to be satisfactory as they avoid a transcutaneous tube connection that has to be continuously maintained and they do not handicap the patient. However, in order to implant the dimensionally stable reservoir, an operation under local anaesthetic or even general anaesthetic is needed which in turn brings with it new and not inconsiderable risks such as infections and surgical bleeding. Furthermore dimensionally stable reservoirs cannot as a rule be used immediately after implantation because of the postoperative swelling of the wound.

OBJECT OF THE INVENTION

It is therefore an object of the invention to provide a catheter system for introducing substances into body cavities and vessels that not only avoids the risks associated with conducting the substance through the skin but also those risks which result from the surgical implantation of the reservoir. In addition, because it weighs less than the dimensionally stable reservoir, the system should have a much smaller tendency to spontaneous perforation through the skin of the patient.

SUMMARY OF THE INVENTION

The invention is based on the idea of providing an artificial access to the vessels and body cavities which can be brought under the skin solely by perforation, i.e. with minimal intervention and without a surgical operation. This object is achieved according to the invention with a catheter system of the kind mentioned in the introduction, by making the reservoir of variable volume so that it can be implanted having a small volume and after being implanted can be adjusted, for example pneumatically, hydraulically or mechanically, to the necessary internal volume.

An operation is no longer necessary to implant the reservoir of the catheter system according to the invention. On the contrary, the reservoir can be introduced under the skin, as in an injection, by means of a needle. An elongated reservoir is particularly advantageous. Because the external diameter is initially small a needle or cannula having a correspondingly small external diameter can be used for implantation. As a result, in contrast to the dimensionally stable reservoirs, it is very much easier to place the reservoir in a favourable position under the skin.

The reservoir according to the invention can be stabilised mechanically by a metal coil or else by an extensible metallic braid in order to keep it dimensionally stable in situ after it has been dilated. For this purpose an internal body made of metal can be embedded in a silicone rubber balloon that can be expanded to a limited extent, the self-sealing properties of which allow the reservoir to be subsequently tapped through the skin of the patient. The metal coil or the metal braid can be expanded purely mechanically by a dilation catheter used for the implantation, and retains its shape because any restoring forces are only small.

Another way of obtaining the required dimensional stability of the reservoir inserted by perforation is to effect the final chemical polymerisation of a plastics material only after implantation, for example by way of percutaneous radiation. In this case also, the reservoir or a coil or a metal braid arranged therein is advantageously dilated by means of a balloon catheter inserted into the reservoir which is removed after serving its purpose.

The connection between the reservoir implanted purely by perforation and the catheter, likewise introduced by perforation into, e.g., central vessels, the abdominal cavity or the spinal cord canal, is effected by a conventional crimp connection. Thus both the transitions between the reservoir and catheter and also the surfaces of the reservoir and the catheter are so smooth that no scar connection with their surroundings is formed. This enables the entire system to be removed through the common perforation point used for positioning the reservoir and the catheter, and at which the crimp connection was sunk under the skin of the patient, by simply pulling.

At the present time the fields of application contemplated for this kind of extremely infection-safe artificial access to vessels, the abdominal cavity and the spinal cord canal are:

1. Intravenous and intra-arterial systemic and regional chemotherapy of individual organs.
2. Long-term artificial feeding.
3. Intravenous and intra-arterial treatment of patients at high risk, for example after bad burns.
4. Chronic out-patient dialysis through the peritoneum. out-patients for pain by catheters near the
5. Treating out-patients for pain by catheters near the spinal cord.

BRIEF DESCRIPTION OF THE DRAWINGS

The invention will now be described in more detail with reference to an exemplary embodiment shown in the drawings, in which.

DETAILED DESCRIPTION OF A PREFERRED EMBODIMENT OF THE INVENTION

Figure 1:
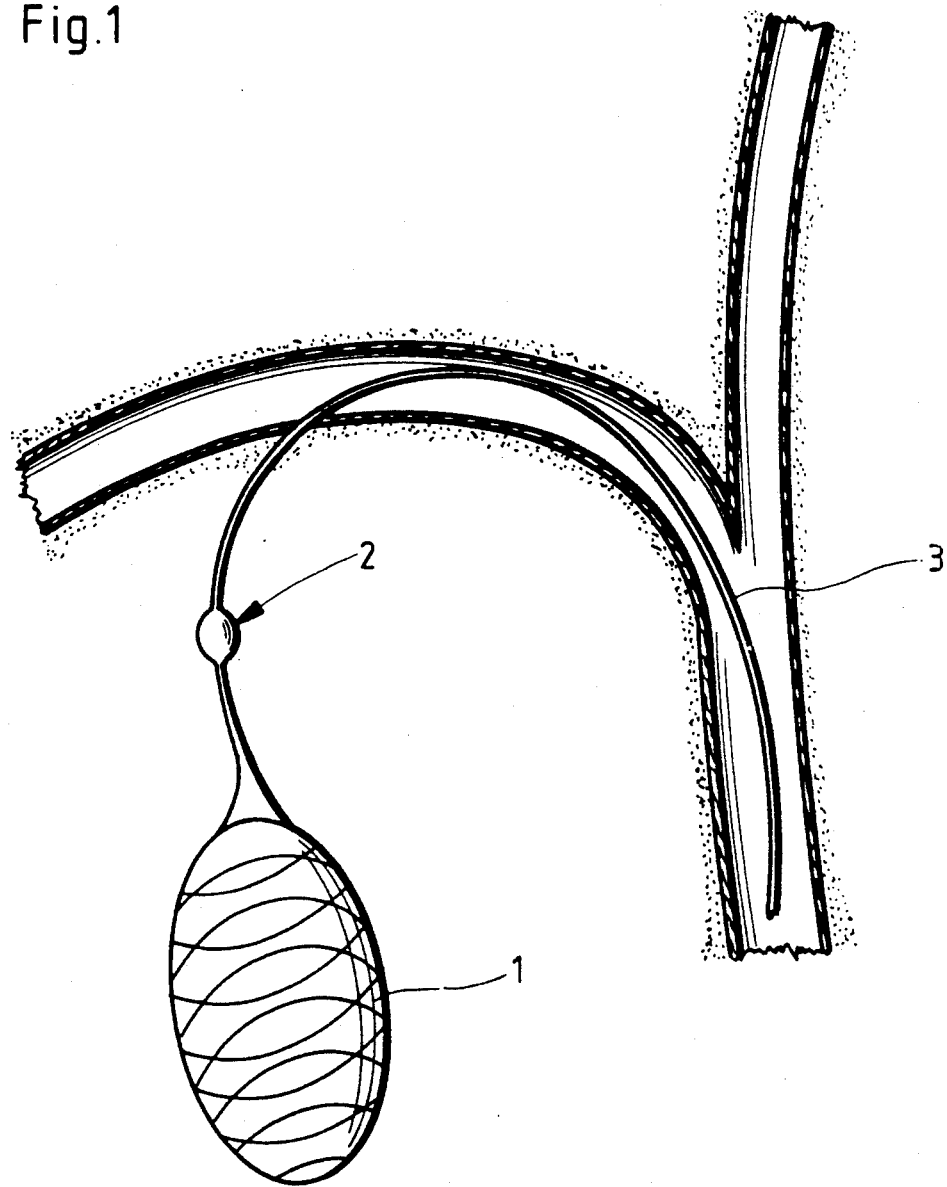
FIG. 1 shows diagrammatically a catheter system according to the invention after implantation.
Figure 2:
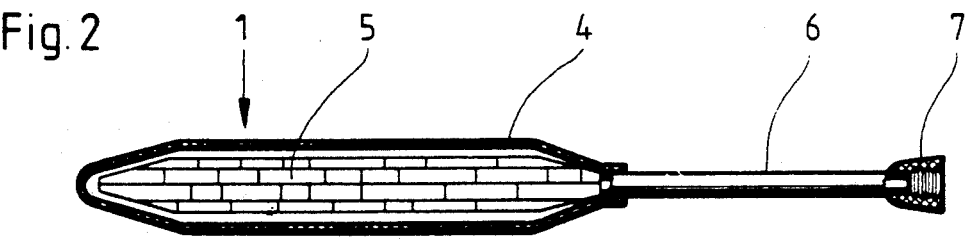
FIG. 2 shows a reservoir before expansion.

A reservoir 1 is connected by a coupling 2 to a catheter 3 which extends, for example, through the vena subclavia (subclavian vein) into the vena cava superior (upper caval vein). The liquid from the reservoir 1 enters the vena cava through the catheter 3 in the region below the vena jugularis interna (inner jugular vein).

The reservoir 1 consists of a balloon-like outer cover 4, for example of an extensible but strong silicone plastics material or silicone rubber. Within the cover 4 there is a metal braid or a metal coil which can be extended but has little or no elasticity, so that it retains its shape after expansion and thereby determines the internal volume of the cover 4 of the reservoir 1. A flexible catheter tube 6 is connected in a liquid-tight manner to the cover 4 to form an extension. At the free end of the catheter tube 6 there is a coupling piece 7 for attaching the catheter 3.

Figure 3:
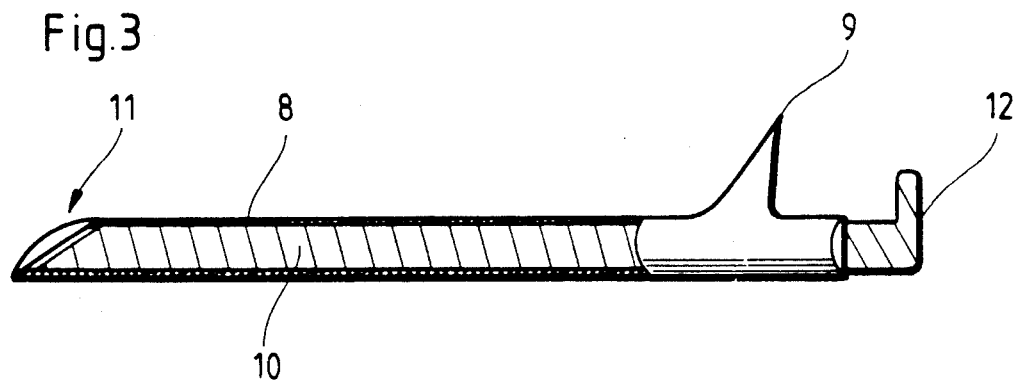
FIG. 3 shows a cannula serving to implant the reservoir.

FIG. 3 shows a cannula needle 8 which is inserted through the skin of the patient into the fatty tissue where it punches out a substantially cylindrical piece of the fatty tissue so that a corresponding cavity results into which the not yet expanded reservoir 1 is subsequently introduced. For easy and safe handling the cannula needle 8 is provided with a handle 9. To push the punched-out piece of fatty tissue from the cannula needle 8 a plunger 10 is provided which has a thumb piece 12 at its end remote from a cutting edge 11. The plunger 10 can subsequently also be used to introduce and position the reservoir 1.

Figure 4:
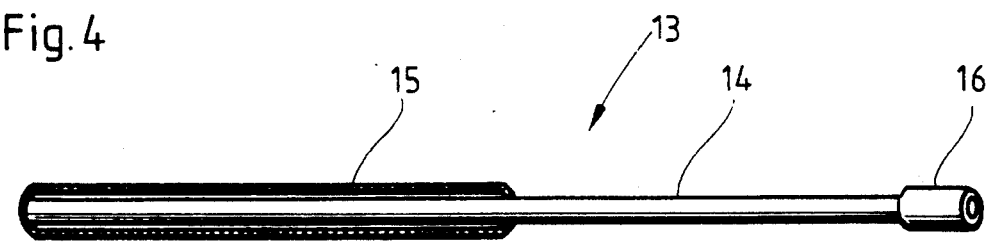
FIG. 4 shows a balloon catheter serving to extend the reservoir.
Figure 5:
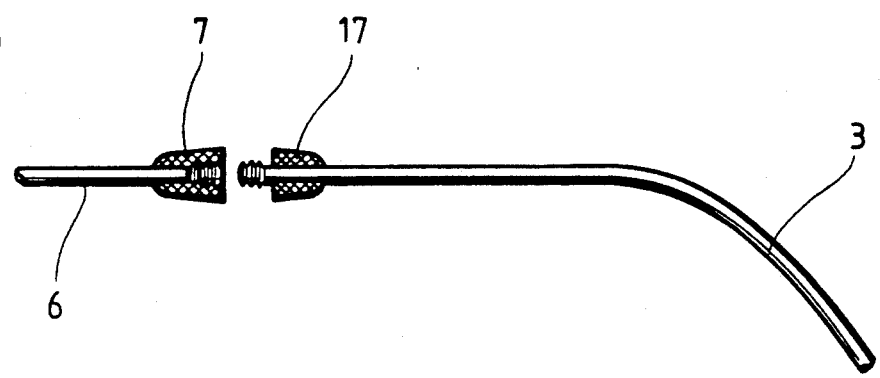
FIG. 5 shows a coupling for connecting the reservoir and catheter.

Serving to expand the reservoir 1 deposited in the fatty tissue is a balloon dilation catheter 13, shown in FIG. 4, consisting of a catheter tube 14 which is surrounded along part of its length by a balloon 15. The connection between the catheter tube 14 and the balloon 15 is designed so that exchange of air is possible in both directions between the catheter tube 13 and the balloon 15 surrounding it, but the air cannot escape outwards from the balloon 15 or from its connection with the catheter tube 14. At the free end of the catheter tube 14 there is an extension 16 which serves to supply air into the catheter tube 14, for example by means of a one-way syringe.

The flexible catheter tube 6 coming from the reservoir 1 can be connected to a coupling piece 17 of the continuing catheter 3 by means of a coupling piece 7. At least one of the coupling pieces 7, 17 can be connected in a friction fitting or positive manner by means of a crimp connection to the associated catheter tube 3 so that the length of one or both of the catheter tubes 3, 6 can be suitably adjusted.

By a conventional perforation method the free end of the catheter 3 can be brought to the point at which the liquid emerging from it is to be applied. The coupling piece 17 connected to the catheter 3 is then brought into a position in which it can be easily connected to the coupling piece 7 of the reservoir 1.

The reservoir 1 is then implanted. For this purpose the cannula needle 8 is brought through the skin of the patient into a position, in particular within a fatty tissue region of the patient, in which the reservoir 1 can be connected to the coupling piece 17 of the catheter 7 by way of the coupling piece 7. The reservoir 1 is introduced through the cannula needle 8. Prior to this however the cylindrical piece of fatty tissue punched out of the fatty tissue of the patient by the cannula needle 8 is either pushed out of the cannula 8 into the body of the patient by means of the plunger 10, or the cannula needle 8 is temporarily removed from the perforation passage, the cylinder of fatty tissue ejected from the cannula needle 8 by means of the plunger 10 and the cannula needle 8 is reinserted into the perforation passage. The reservoir 1 is then inserted into the now empty cannula needle 8 and, if necessary with help from the plunger 10, is brought into the desired position within the fatty tissue. For this purpose the coupling piece 7 can point towards the skin or else to the inside of the body if this is advantageous. After positioning the reservoir 1 the cannula needle 8 is removed.

The balloon dilation catheter is then introduced into the reservoir 1 through the coupling piece 7 and the catheter tube 6. By forcing air or another fluid via the connection piece 16 into the balloon dilation catheter 13, the balloon 15 thereof is inflated with the result that the diameter of the metal braid 5 is increased and thus the internal volume of the reservoir 1 is adjusted.

The dilation of the reservoir 1 can readily be followed radiographically. After removing the balloon dilation catheter from the reservoir 1, the reservoir 1 is connected to the catheter 3 by means of the coupling 2.

Filling or refilling of the reservoir is done by a hollow needle which is passed through the skin of the patient into the reservoir 1. The cover 4 of the reservoir is therefore designed so that it can withstand repeated perforation without leaks occurring.

The catheter system according to the invention can be used not only for injecting substances but also for flushing body cavities or vessels. For this purpose it is only necessary to fill and empty the reservoir 1 periodically.

The volume-adjustable reservoir 1 enables the totally implantable catheter system to be introduced into the body of a patient virtually without risk through relatively harmless perforation and without surgery which would otherwise have been necessary.

A particular advantage of the catheter system according to the invention is that owing to the design and the simple implantation technique, problem-free extraction of the system is possible if infection should occur or in case it is no longer needed.

What is claimed is:

1. A catheter system comprising a reservoir and at least one catheter attached thereto for applying treating agents, wherein the reservoir is of a variable volume and consists of an extensible and hardenable plastic material.

2. A catheter system according to claim 1, wherein said reservoir is elongated.

3. A catheter system according to claim 1, wherein the wall of said reservoir consists of a material that can be repeatedly punctured.

4. A catheter system according to claim 1, wherein said reservoir is elongated.

5. A catheter system according to claim 1, wherein the wall of said reservoir consists of a material that can be repeatedly punctured.

6. A catheter system comprising:
   a reservoir;

at least one catheter attached thereto for applying treating agents, the reservoir being of variable volume; and a balloon catheter shaped so as to be fittable inside said reservoir.

7. A catheter system according to claim 6, wherein said reservoir is elongated.

8. A catheter system according to claim 6, wherein the wall of said reservoir consists of a material that can be repeatedly punctured.

9. A catheter system comprising:

a reservoir;

at least one catheter attached thereto for applying treating agents, the reservoir being of variable volume;

an extensible metal body arranged within said reservoir; and a balloon catheter shaped so as to be fittable inside said reservoir and said extensible metal body.

10. A catheter system according to claim 9, wherein said reservoir is elongated.

11. A catheter system according to claim 9, wherein the wall of said reservoir consists of a material that can be repeatedly punctured.

* * * * *